United States Patent [19]

Matsuda et al.

[11] Patent Number: 4,780,410

[45] Date of Patent: Oct. 25, 1988

[54] SANDWICH ENZYME IMMUNOASSAY FOR PIVKA-II WITH MONOCLONAL ANTI-PIVKA-II ANTIBODY

[75] Inventors: Ichiro Matsuda; Kunihiko Motohara, both of Kumamoto, Japan

[73] Assignee: Eisai Co., Ltd., Tokyo, Japan

[21] Appl. No.: 643,223

[22] Filed: Aug. 21, 1984

[30] Foreign Application Priority Data

Sep. 13, 1983 [JP] Japan ................................ 58-167458

[51] Int. Cl.[4] .................. G01N 33/53; G01N 33/535; G01N 33/577
[52] U.S. Cl. .......................................... 435/7; 435/13; 435/172.2; 435/240.27; 435/810; 436/548; 436/825; 530/387; 935/110
[58] Field of Search ...................... 260/112 R, 112 B; 435/7, 13, 172.2, 240, 810, 240.27; 436/531, 548, 811, 825; 935/110; 530/387

[56] References Cited

U.S. PATENT DOCUMENTS 4,376,110  3/1983  David et al. ...................... 436/513

OTHER PUBLICATIONS

Tai, M. M. et al., J. Biol. Chem., 255 (7), 2790-2795 (1980).
Furie, B. et al., J. Biol. Chem., 253 (24), 8980-8987 (1980).
Owens, J. et al., J. Biol. Chem., 259 (22), 13800-13805 (1984).
Stenflo, J. et al., Proc. Nat. Acad. Sci. U.S.A., 71 (7), 2730-2733 (Jul. 1974).
Nelsestuen, G. L. et al., J. Biol. Chem., 249 (19), 6347-6350 (Oct. 10, 1974).
Tuhy, P. M. et al., Biochemistry, 18 (26), 5842-5848 (1979).
Kohler, G. et al., Nature, 256, 495-497 (Aug. 7, 1975).
Blanchard et al., "The New England Journal of Medicine," vol. 305, No. 5, (Jul. 1981), pp. 242-248.
Lewis et al. "Biochemistry," vol. 22, No. 4 (1983), pp. 948-954.

Primary Examiner—Sidney Marantz
Attorney, Agent, or Firm—Flynn, Thiel, Boutell & Tanis

[57] ABSTRACT

A method for use in the assay of PIVKA-II by the enzyme immunoassay using the two antibody-sandwiching method, characterized by using a monoclonal anti-PIVKA-II antibody as solidified antibody for said assay.

4 Claims, 4 Drawing Sheets

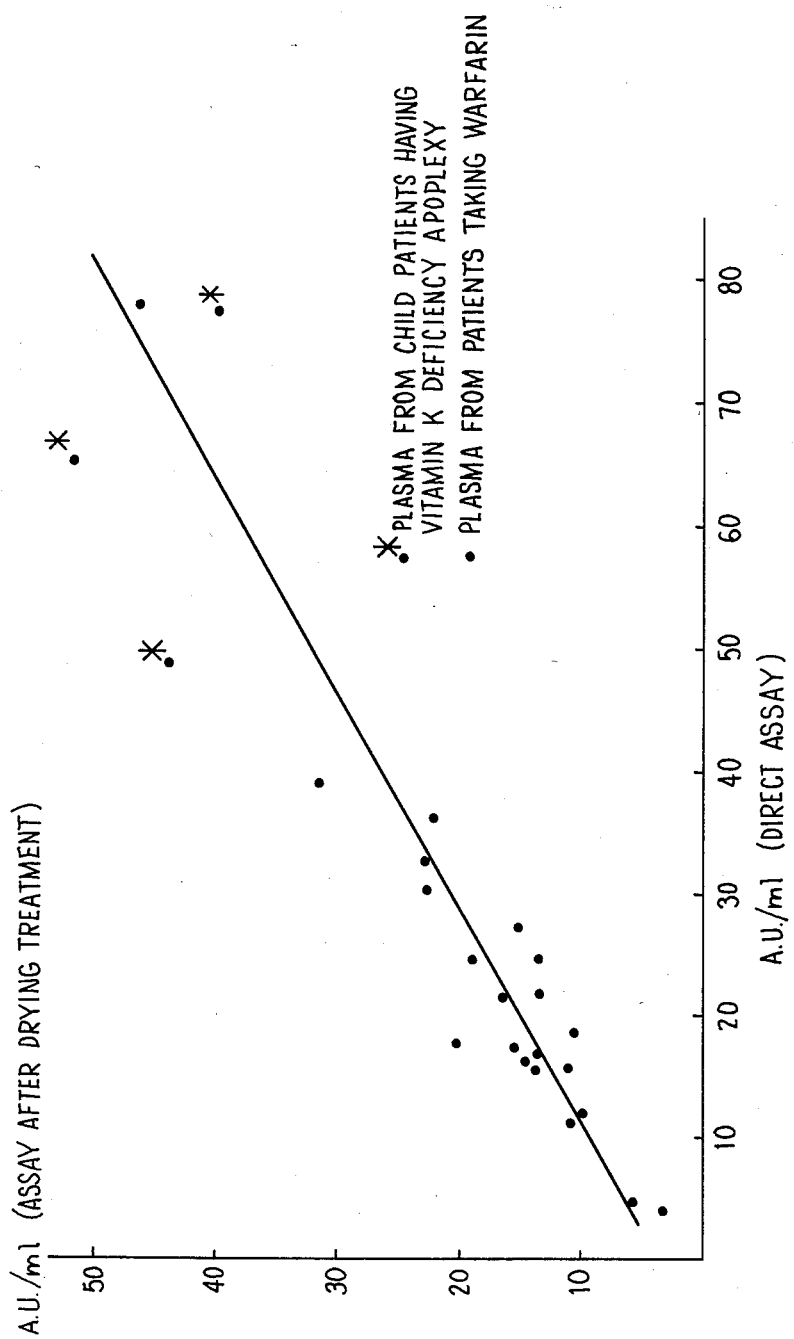

SANDWICH ENZYME IMMUNOASSAY FOR PIVKA-II WITH MONOCLONAL ANTI-PIVKA-II ANTIBODY

The present invention relates to a method and a reagent for use in the assay of PIVKA-II, more particularly to a method and a reagent for use in the assay of PIVKA-II by the enzyme immunoassay using the two antibody-sandwiching method. PIVKA-II is a prothrombin precursor itself or a prothrombin precursor having glutamic acid residues incompletely carboxylated. On the other hand, a prothrombin precursor having glutamic acid residues completely carboxylated is called normal prothrombin. In other words, therefore, PIVKA-II can be regarded as a normal prothrombin having γ-carboxyglutamic acid residues decarboxylated. Actually, for example, in the blood, a plurality of substances which are concordant with the above definition but different in the degree of carboxylation are present in admixture. Such a mixture may be referred to as PIVKA-II comprehensively. As the principal object of the present invention is to assay PIVKA-II contained in the blood, PIVKA-II in the present specification includes the PIVKA-II in its comprehensive meaning so long as it is not particularly annotated. On the other hand, it is known that PIVKA-II appears when vitamin K is insufficient physiologically or clinically, or when the action of vitamin K is inhibited by the administration of vitamin K inhibitors. More particularly, glutamic acid residues present in prothrombin precursor are carboxylated into activated normal prothrombin in the presence of vitamin K and carboxylase, but the carboxylation is incompletely effected when vitamin K is insufficient or inhibited, which results in the appearance of PIVKA-II in the blood. PIVKA-II is the abbreviation of Protein Induced by Vitamin K Absence-II, which was named from the abovementioned physiological point of view. The following references are listed regarding PIVKA-II and the relationship between PIVKA-II and vitamin K.

(1) Stenflo, J., Fernlund, P., Egan, W., and Roepstorff, P. Vitamin K dependent modification of glutamic acid residues in prothrombin. Proc. Natl, Acad. Sci. USA. (1974) 71, 2730-3.

(2) Nelsestuen, GL., Zytkovicz, TH., and Howard, JB. The mode of action of vitamin K: identification of γ-carboxyglutamic acid as a component of prothrombin. J. Biol. Chem. (1974) 249, 6347-50.

(3) Magnusson, S., Sottrup-Jensen, L., Petersen, TE., Morris, HR., and Dell, A. Primary structure of the vitamin K-dependent part of prothrombin. FEBS Lett. (1974) 44, 189-93.

It is clinically important to discover vitamin K deficiency, particularly vitamin K deficiency apoplexy of babies, such as neonatal apoplexy, in its early stage by the assay of vitamin K in the blood.

Hepaplastin test (HPT) is often employed at present for this prognosticative and preventive assay. However, as physiological decrease of values caused by protein coagulation is recognized in babies, hepaplastin test does not always indicate vitamin K deficiency. It is necessary, therefore, to directly determine PIVKA-II quantitatively to establish a more suitable and exact method of prognostication and prevention. Two-dimensional cross immunoelectrophoresis (CIEP) is recommended to put to practical use for this purpose. However, this method is disadvantageous for practical use in clinical examinations because operations are too complicated to simultaneously treat large quantities of specimens. In order to establish a simpler method, it is preferable to practise radioimmunoassay or enzyme immunoassay. For example, the following literature (4) indicates a method of performing radioimmunoassay:

(4) Rita A., Blanchard, et al., Acquired vitamin K-dependent carboxylation defficiency in liver disease:

New England J. Medicine, Vol. 305, No. 5 (1981) 242-248.

However, this method employs competitive radioimmunoassay and is not yet of practical use. Moreover, a process for the purification of PIVKA-II -specific antibody is troublesome in this method and only limited amounts of purified antibodies are obtained.

Under these circumstances, the present inventors have continued studies in search for a practical method of an exact and simple assay of PIVKA-II, particularly of a simultaneous treatment of large quantities of specimens in clinical examinations. In pediatric clinical examinations of, for example, collected plasmas, specimens are usually pre-treated by drying with filter paper before the assay. The demanded method of an exact and simple assay of PIVKA-II must be suited to said pretreatment, too. The inventors have accomplished the present invention as the result of intensive studies, taking these circumstances into consideration, based on the findings that an enzyme immunoassay using the two-antibody-sandwiching method must be employed and that a monoclonal antibody PIVKA-II antibody must be used as the solidified antibody in the two-antibody-sandwiching method.

More particularly, an object of the present invention is to make possible an exact and simple assay of PIVKA-II in specimens even if the quantities of the specimens are large and the specimens have been subjected to drying pretreatment before the assay, and the present invention provides a method of an enzyme immunoassay characterized by employing the two-antibody-sandwiching method, in which a monoclonal anti-PIVKA-II antibody is used as the solidified antibody for the attainment of the object.

The present invention will now be described in more detail.

The monoclonal anti-PIVKA-II antibody of the present invention is prepared, for example, as follows:

First of all, PIVKA-II is prepared. The plasmas of patients who are taking warfarin are treated with $BaSO_4$ and $BaCO_3$ so that prothrombin is adsorptively removed, and then ion-exchanged with DE-52 CELLULOSE (cellulose chromalography). The plasmas are finally adsorbed on an affinity column in which the monoclonal antibody of the part in common to both of normal prothrombin and PIVKA-II is used. The adsorbate is eluted with 4M guanidine hydrochloride, dialyzed, and concentrated, yielding PIVKA-II.

50 μg of the thus prepared PIVKA-II is abdominally administered to BALB/C mice with the same volume of Freund's complete adjuvant. After two weeks, 15 μg of PIVKA-II is further administered to the caudal vein and, after three days, the spleen cells are extracted and immediately subjected to cell-fusion with tumor cell strain P3U1 in the presence of polyethylene glycol 4000 according to the method of Watanabe et al. (See the literature (5) cited below). Cloning is then performed three times by the limiting dilution. The cloning is made using, for example, MONO-AB-SCREEN G kit (monoclonal antibody cloning kit, Zymed, So. San Francisco, Calif.), with the selection of such a well that does not react with normal prothrombin but reacts only with decarboxylated prothrombin. The monoclonal anti-PIVKA-II antibody-producing cell lines are established by further confirming that the well reacts with native abnormal prothrombin. The normal and decarboxylated prothrombins to be used here can be prepared by the methods described in the following literature (6) (by Shapiro et al.) and (7) (by Tuhy et al.). Normal prothrombin is prepared, for example, as follows.

DE-52 CELLULOSE and citric acid are added to fresh frozen plasma. The residue is washed after stirring the mixture, eluted with a citrate buffer solution, adsorbed by the addition of $BaCl_2$, again eluted with a citrate buffer solution and salted out by the addition of saturated ammonium sulfate. The salted substance is suspended in a citrate buffer solution, dialyzed, and gel-filtered through a SEPHADEX G-100 (Pharmocia, Piscataway, N.J.) column to collect the fractions corresponding to the predetermined peak. The obtained fractions are treated with a DE-52 CELLULOSE column and eluted with a citrate buffer solution having a concentration gradient of NaCl to obtain the desired normal prothrombin.

(5) Watanabe and Kaitsu: Cell fusion method of lymphocytes Biomedical Sciences Vol. 1, No. 1, 46-51 (1980).

(6) Shapiro, S. S., and D. E. Waugh: The purification of human prothrombin, Thromb. Diath Haemorph., 16, 469-490 (1966).

(7) Tuhy, P. M., Bloom, J. W., and Mann, K. G: Decarboxylation of bovine prothrombin fragmen I and prothrombin, Biochemistry (1939) 18, 5842-8.

The enzyme immunoassay employing the two-antibody-sandwiching method of the present invention is practised for example as follows.

The entire assay system is composed of a solid phase, a monoclonal anti-PIVKA-II antibody (primary antibody) for solid-phase coating, a standard antigen or plasma specimen, a labelling antibody (secondary antibody), an enzyme, and a substrate. A well of a microtiter plate for the enzyme immunoassay can be used as the solid phase. Before the assay, a monoclonal anti-PIVKA-II antibody is dissolved in a carbonate buffer solution (pH 8.5). The solution charged into a polystyrene well for the enzyme immunoassay is left to stand overnight at 4° C. so that the surface of the solid phase is coated. However, as some portions of the surface are not coated with the monoclonal antibody, these portions are coated with bovine serum albumin which has been dissolved in a phosphate buffer solution, charged into a well and left to stand in the same manner as above.

A plasma of a patient having a predetermined concentration is used as the standard antigen. The standard antigen is dissolved in a phosphate buffer solution containing bovine serum albumin (pH 7.4), charged into the coated well for reaction, and washed, An appropriate anti-human prothrombin antibody, for example, anti-human prothrombin rabbit IgG, is selected as the labelling antibody (secondary antibody). The anti-human prothrombin rabbit IgG can be prepared as follows.

First, human prothrombin is prepared from fresh frozen plasma according to the method of Shapiro et al. mentioned above. A rabbit is immunized with the obtained human prothrombin. The blood is collected from the rabbit and ammonium sulfate is added to the serum of the blood. The serum is salted out, dialyzed, and thereafter ion-exchanged with DE-52 cellulose. The ion-exchanged product is adsorbed on a human prothrombin affinity column and then eluted with 4M guanidine hydrochloride, yielding the desired anti-human prothrombin rabbit IgG. The human prothrombin affinity column is prepared by activating CNBr by the ordinary method and adding huma prothrombin dissolved in a phosphate buffer solution thereto to effect adsorption.

The enzyme to be used here includes alkali phosphatase, glucose oxidase, peroxidase and beta-oxidase. Before the assay, the enzyme is bound to the labelling antibody to form a conjugate with a binder such as glutaraldehyde. This conjugate can be preliminarily prepared as a part of the reagents for the performance of the assay of the present invention. The labelling can be carried out according to, for example, the following method of the literature (8) (by Nakane et al.).

(8) P. K. Nakane, R. M. Nakamura, W. R. Dito, and E. S. Tucker: Preparation and standarization of enzyme labeled conjugate. Immunoassaies in the clinical laboratory (3ed) p. 81, Alan R Liss Inc. NY An appropriate substrate is used corresponding to the enzyme selected. For example, when alkali phosphatase is selected as enzyme, p-nitrophenyl phosphate is used as substrate, while when peroxidase is selected, ABTS (2,2'-azinobi(3'-ethylbenzothiazolinesulfonic acid)) is used.

The assay is carried out according to the ordinary processes of an enzyme immunoassay using the two-antibody-sandwiching method. In more detail, as described in the examples below, the standard antigen or the plasma specimen is added to the coated well and incubated, followed by the addition of the enzyme-labelled antibody, and again incubated, and finally the substrate is added and further incubated. After the reaction is terminated, the amount of the decomposed substrate is measured by a spectrophotometer.

The reagent for use in the assay of the present invention is a reagent to be directly used in the performance of the assay of the present invention and its object is the same as that of the method of the assay of the present invention. The practical embodiment of the reagent for the assay of the present invention is as follows.

The reagent for use in the assay of the present invention is a kit containing as an essential component a monoclonal anti-PIVKA-II antibody and comprises this antibody alone or a combination with one to five articles arbitrarily selected from the group consisting of a solid phase, standard antigen, anti-human prothrombin antibody for labelling, enzyme, and a substrate. In the embodiment of the reagent for use in the assay of the present invention when a solid phase is contained in the kit, it may be provided as coated with the monoclonal anti-PIVKA-II antibody. Similarly, when an anti-human prothrombin antibody and an enzyme are contained in the kit, they may be provided as a conjugate. Moreover, an appropriate antigen-diluting solution, reaction-diluting solution, substrate-dissolving solution, reaction-terminating solution, or the like are optionally added to the kit for the convenience in the performance of the assay. However, these additional provisions are not to limit the scope of the present invention.

The advantages of the present invention are summarized as follows.

First, the present invention, wherein an enzyme immunoassay is performed using the two-antibody-sandwiching method, is simple and easy in operation, and therefore large quantities of specimens can be treated simultaneously, which is of great value for the practical use in clinical examinations.

Secondly, although ordinary antibodies obtained by the immunization with PIVKA-II intersects normal prothrombin because of the extreme similarity in molecular structures of PIVKA-II and normal prothrombin, such intersection can be avoided in the present invention wherein a monoclonal anti-PIVKA-II antibody is used as solidified antibody. Therefore, the calibration with respect to PIVKA-II is very high as shown in the examples of experiments described below, and good correlation is found between the assay of the present invention and the two-dimensional cross immunoelectrophoresis (CIEP) which has been recommended as a method of exactly determining the positivity and negativity of PIVKA-II.

The most remarkable advantage of the present invention is that the plasma specimens can be calibrated if they are pre-treated before the assay by, for example, drying with dry filter paper for the screening of congenital dysbolism and the same results as when the plasma specimens are directly assayed are obtained.

BRIEF DESCRIPTION OF THE DRAWINGS

FIG. 4 corresponds to the FIG. 4 described in the Results of Experimental Example 4 and graphically represents the correlation between the measured values in the direct assay of the plasma specimens and those in the assay after the drying treatment of the same.

The advantages of the present invention will be more readily understood by the following experimental examples.

EXPERIMENTAL EXAMPLE 1

Specimens and Method

Three types of specimens were prepared: prothrombin-free plasma in which normal prothrombin has been preliminarily removed by adsorption (Specimen a) was prepared by adding $BaSO_4$ and $BaCO_3$ in an amount of 100 mg each per ml of the normal plasma and stirring the mixture for 120 minutes. Sample b, in which normal prothrombin obtained by the method described in Example 1 below was added to Specimen a, and Specimen c, in which PIVKA-II was added to Specimen a, were then prepared. The three specimens were charged into wells coated with monoclonal anti-PIVKA-II antibodies with different amounts of protein in the wells, and assayed according to the same procedures as described in Example 4 below.

Results

Figure 1:
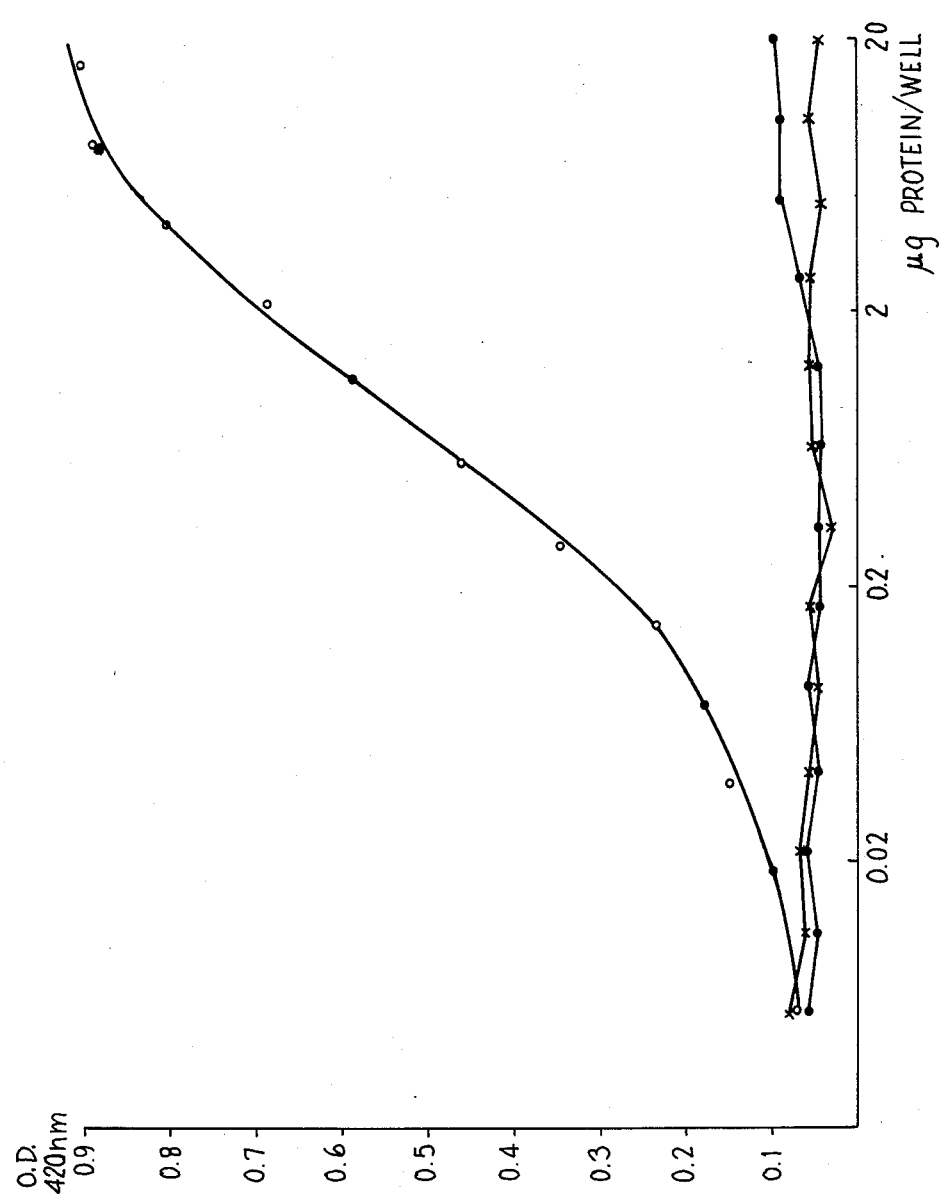
FIG. 1 corresponds to the FIG. 1 described in the Results of Experimental Example 1 and graphically represents the relationship between the amount of the protein and the measured values obtained in an embodiment of the method of the assay of the present invention.

The results are shown in FIG. 1. The abscissa stands for the amount of PIVKA-II or of prothrombin protein (μg) per well and the ordinate for the value of $OD_{420nm}$. The line X in the figure stands for the results with Specimen a, the line ● for Specimen b, and the line ○ for Specimen c. It is understood from FIG. 1 that the present invention has high specificity and excellent calibration with respect to PIVKA-II.

EXPERIMENTAL EXAMPLE 2

Specimens and Method 32 specimens of the plasmas from the patients who were taking warfarin and 3 specimens of the plasmas from the child patients of vitamin K deficiency apoplexy were prepared and subjected to the negative or positive determination by the two-dimensional cross immunoelectrophoresis and the assay of the present invention in the same manner as described in Example 4 below. 25 specimens of the plasmas from healthy adults were also subjected to the assay of the present invention in the same manner as described in Example 4. 16 specimens of the plasmas from the patients taking warfarin which showed a prothrombin period of 20 seconds or more were pooled and removed of normal prothrombin by the pretreatment with $BaSO_4$ and $BaCO_3$ PIVKA-II as standard antigen was prepared and quantitatively determined by the Laurel method. The results were calculated based on the definition that the amount of the antigen corresponding to 1 μg of normal prothrombin was 1 A.U. The calibration curve between the values of A.U./ml and the values of $OD_{420nm}$ obtained by the method of the present invention had been preliminarily prepared. The CV on this calibration curve within the range of the assay was 0.015 to 0.06.

Results

Figure 2:
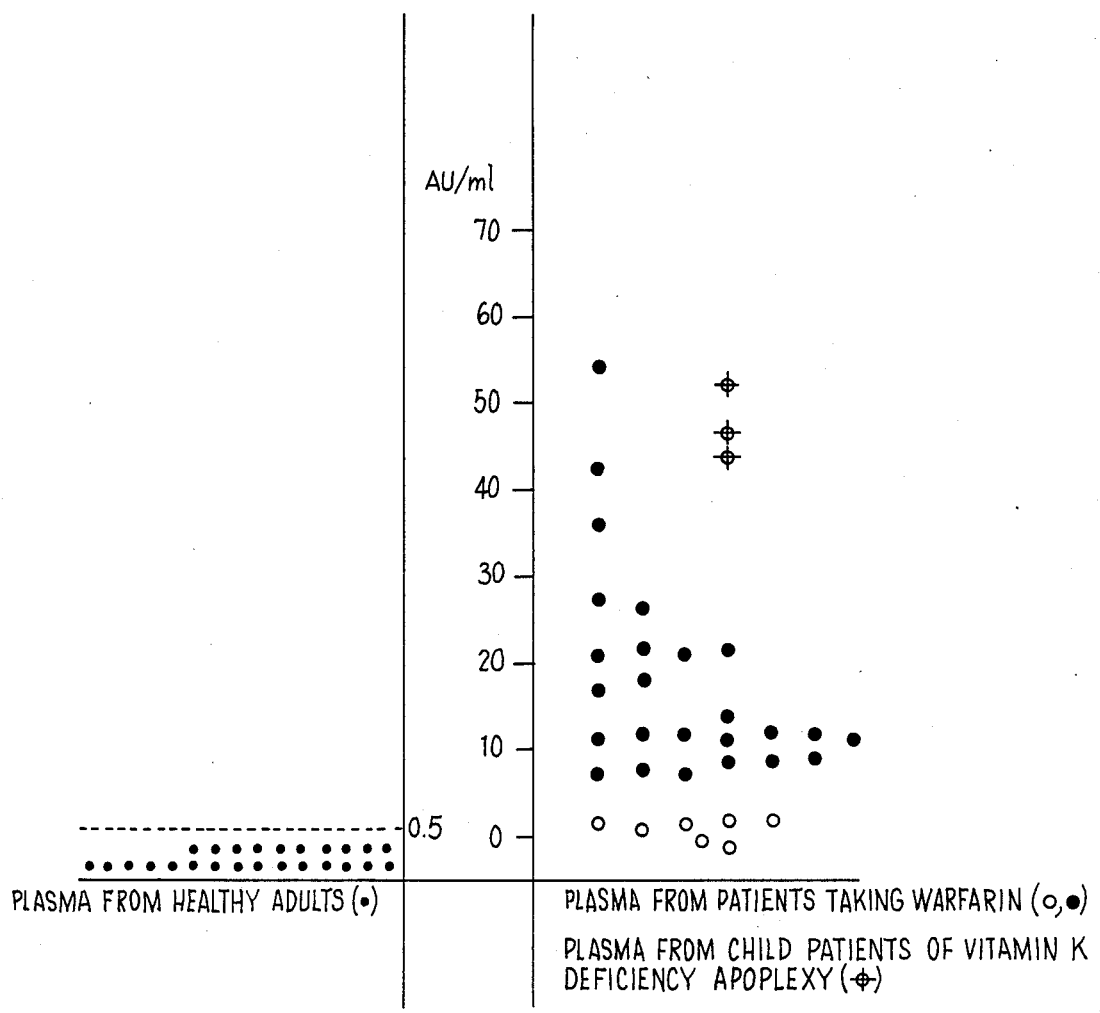
FIG. 2 corresponds to the FIG. 2 described in the Results of Experimental Example 2 and graphically represents the correlation between the assay of the present invention and the two-dimensional cross immunoelectrophoresis.

The results are shown in FIG. 2. The results with the plasmas from the healthy adults are shown in the left column and those from the patients taking warfarin and from the child patients of vitamin K deficiency apoplexy in the right column. The marks in the right column stand for the results with the plasmas from the child patients of vitamin K deficiency apoplexy, the marks ● for the results with the plasmas from the warfarin-taking patients which were determined as positive by CIEP, and the marks ○ for the results with the plasmas from the warfarin-taking patients which were determined as negative by CIEP. It is understood from FIG. 2 that a good correlation is present between the results of the assay of the present invention and those of CIEP, which has been recommended as a method for exact determination and that the assay of the present invention can be substituted for CIEP.

EXPERIMENTAL EXAMPLE 3

Specimens and Method

O-type red blood cells were added to the plasmas deprived of normal prothrombin described in the Specimens and Method of Experimental Example 2 in the ratio of 55:45. A dry filter paper for congenitus dysbolism screening was impregnated with said red blood cell-containing plasmas, dried for 6 hours at room temperature, and punched out to the circles of 5 mm is diameter. Eight of the punched circles were selected, 0.3 ml of a phosphate buffer solution containing bovine serum albumin being added thereto for elution, as samples of standard antigen. The obtained standard antigen was charged into the wells in a variety of concentration subjected to the assay of the present invention in the same manner as described in Example 4 below.

Results

Figure 3:
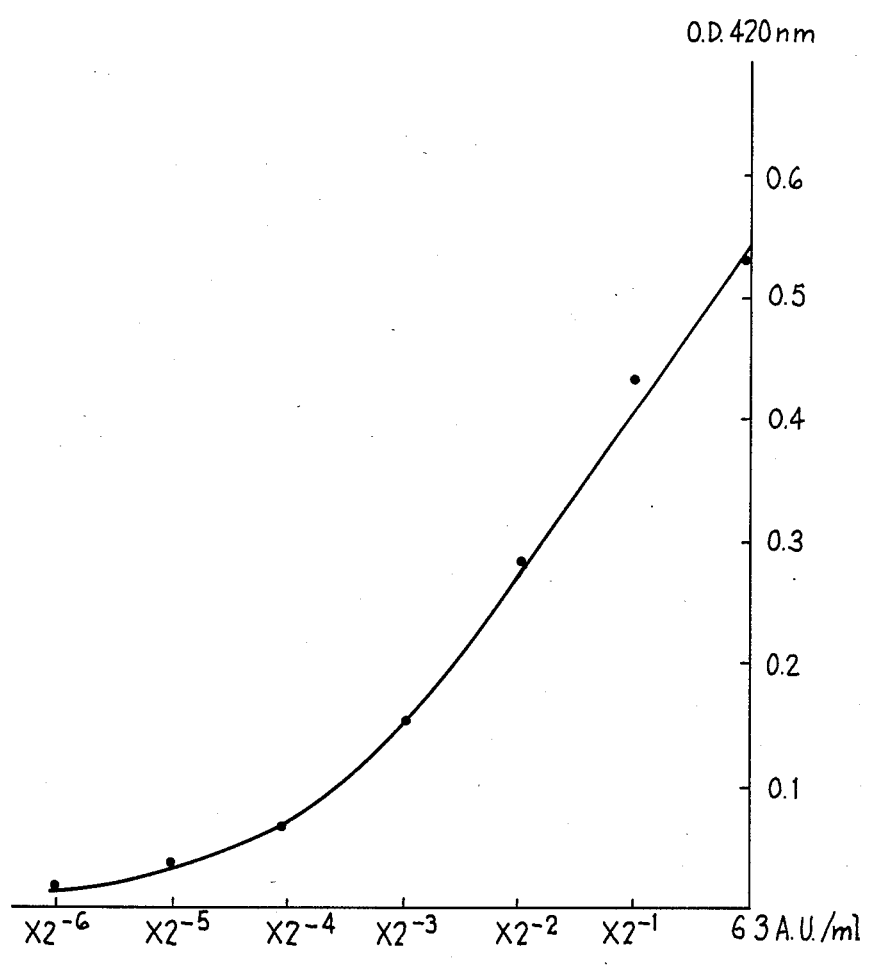
FIG. 3 corresponds to the FIG. 3 described in the Results of Experimental Example 3 and graphically represents the calibration curve in case of the pre-treatment of plasma specimens with filter paper for drying.

The results are shown in FIG. 3. FIG. 3 shown the calibration curve, the CV of which within the range of 63 to $63 \times 10^{-3}$ A U./ml was 0.063 to 0.092. It is understood from FIG. 3 that the calibration properties of the assay of the present invention is not lost if the specimens are pretreated with filter paper for drying.

EXPERIMENTAL EXAMPLE 4

Specimens and Method 21 specimens of the plasmas from the warfarin-taking patients and 3 specimens from the child patients of vitamin K deficiency apoplexy were prepared. Both of the direct assay in the same manner as described in Example 4 and the pretreatment with filter paper for drying in the procedures described in Specimens and Method of Experimental Example 3 followed by the assay described in Example 4 were performed with said specimens.

Results

The results are shown in FIG. 4. The abscissa of FIG. 4 stands for the values of the direct assay and the ordinate for the values of the assay after the pre-treatment with filter paper for drying. The plots with the mark * are the results of the assay on the plasmas from the child patients of vitamin K deficiency apoplexy. The formula represented by the regression line in the figure is $Y=0.57X+3.67$ and the correlation coefficient $\gamma$ thereof is 0.954 ($P<0.005$). It is understood from FIG. 4 that there is a good correlation between the two values, and therefore when the pre-treatment for drying is carried ou because of the difficulty in collecting plasmas, the same results are obtained as in the direct assa of the plasma specimens.

The present invention will be more readily understood by the following examples.

EXAMPLE 1

A. DE-52 CELLULOSE and 200 ml of a 10 mM sodium citrate solution (pH 7.0) were added to 400 ml of fresh frozen plasma. The mixture was stirred for 5 minutes and centrifuged at 1500 rpm. The residue was flushed three times with 400 ml portions of a 100 mM trisodium citrate solution (pH 7.0). 400 ml of a 500 mM trisodium citrate solution (pH 7.0) was then added for elution, and 2000 ml of a 20 mM trisodium citrate solution (pH 7.0) was further added to the eluate. After 20 g of BaCl₂ was added, th eluate was stirred for 15 minutes and centrifuged at 5000 rpm for 15 minutes. The residue was flushed three times with deionized water and eluted with 40 ml of a 170 mM trisodium citrate solution (pH 7.0). 20 ml of saturated ammonium sulfate was added to the eluate, which was then centrifuged at 3500 rpm for 10 minutes. 60 ml of saturated ammonium sulfate was further added to the supernatant, which was then centrifuged at 9000 rpm for 20 minutes. The residue was suspended in a 10 mM trisodium citrate solution (pH 7.0; containing 250 mM NaCl), dialyzed, and gel-filtered through a SEPHADEX G-100 column. The fractions around the peak were collected, adsorbed on a DE-52 cellulose column, eluted by the concentration gradient from a 20 mM trisodium citrate solution (containing 100 mM NaCl) to a 20 mM trisodium citrate solution (containing 500 mM NaCl), and the fractions around the peak were collected. Purified normal human prothrombin was thus obtained, the final yield thereof ranging from 25 to 35%.

A rabbit was immunized with the thus obtained normal human prothrombin and 35% ammonium sulfate was added to the antiserum thereof. The obtained residue was dialyzed, adsorbed on a DEAE-cellulose column, and treated with a 17 mM phosphate buffer solution (pH 6.8) to collect IgG fractions. On the other hand, normal prothrombin was dissolved in a 10 mM phosphate buffer solution (pH 7.2; containing 130 mM NaCl) so that the concentration of the solution was preliminarily adsorbed on activated CNBr by the ordinary method to prepare a prothrombin affinity column. Said IgG fractions were adsorbed on this prothrombin affinity column and eluted with 4M guanidine hydrochloride to obtain anti-human prothrombin rabbit IgG. Decarboxylated human prothrombin was obtained by decarboxylatng normal human prothrombin by Tuhy's method.

B. BaSO₄ and BaCO₃ were added to the plasmas from warfarin-taking patients in an amount of 100 mg/ml each. After the plasma mixture was stirred for 120 minutes, normal prothrombin was removed by adsorption. The plasma mixture was then ion-exchanged with DE-52 cellulose, adsorbed on an affinity column in which the monoclonal antibodies of the part common to normal prothrombin and PIVKA-II were used, eluted with 4M guanidine hydrochloride, dialyzed, and concentrated to obtain purified PIVKA-II.

50 µg of the thus obtained PIVKA-II was abdominally administered to BALB/C mice (female, 4 weeks of age) with the same volume of Freund's complete adjuvant. After two weeks, 15 µg of PIVKA-II was further administered to the caudal vein. After three days, the spleen cells were extracted and fused with the tumor cell strain P3U1. This cell fusion was effected according to the method of Watanabe et al. using polyethylene glycol 4000. Cloning was then performed three times by the limiting dilution using a 96-well microplate. The decarboxylated human prothrombin described in A and, finally, native PIVKA-II were used in the assay for the cloning. The marks MU-1, MU-2, MU-3, MU-4, and MU-5 were labelled on the cell lines of antibody-producing hybridomas established by the cloning. An RPMI 1640 medium containing 20% FCS and 10% DMSO was used as medium for the maintenance of these cell lines. The samples were frozen at −160° C. and melted at 37° C. The survival of the samples was confirmed by the microscopic observation of morphology and changes in proliferability of the cells with time. Monoclonal anti-PIVKA-II antibodies were obtained from the cell line MU-3 by the ordinary method. The obtained monoclonal anti-PIVKA-II antibodies were prepared as the reagent for use in the assay of the present invention. A combination of the monoclonal anti-PIVKA-II antibody and the antihuman prothrombin rabbit IgG obtained in A was also prepared as a kit of the reagents for use in the assay of the present invention.

EXAMPLE 2

The monoclonal anti-PIVKA-II antibodies obtained in Example 1 was dissolved in a 0.1M carbonate buffer solution (pH 8.5) in a concentration of 10 to 15 µg of the antibodies in 50 µl of the buffer solution, charged into a multiplate for enzyme immunoassay by 100 µl per well, and left to stand overnight at 4° C. Coated solid phases were prepared by flushing the samples once with a 10 mM phosphate buffer solution (pH 7.4; containing 0.2% bovine serum albumin and 0.15 M NaCl), further incorporating therein 1% bovine serum albumin, allowing to stand overnight, and flushing three times with said buffer solution. Enzyme-labelled antibodies were prepared by conjugating peroxidase with the anti-human prothrombin rabbit IgG obtained in Example 1 by the method of Nakane et al. A combination of said coated solid phase and said enzyme-labelled antibody was prepared as a kit of the reagents for use in the assay of the present invention.

EXAMPLE 3

Dry filter paper for screening was further added to the reagent described in Example 2 and prepared as the reagent for use in the assay of the present invention.

EXAMPLE 4

100 µl portions of the plasma specimens were charged into the wells of the coated solid phase obtained in Example 2 and incubated for 24 hours at 4° C. The specimens were flushed three times with a 10 mM phosphate buffer solution (pH 7.4; containing 0.2% bovine seru albumin and 0.15M NaCl) and incubated for 60 minutes at 37° C. with 50 µl of the enzyme-labelled antibody obtained in Example 2 added thereto. The specimens were flushed three times with said buffer solution and left to stand for 30 minutes after the addition of 100 µl of an ABTS solution, and the reaction was terminated by adding 50 µl of 2 mM sodium azide, when the $OD_{420nm}$ was assayed.

The embodiments of the invention in which an exclusive property or privilege is claimed are defined as follows:

1. In a method for assaying for PIVKA-II in a clinical specimen, the improvement comprising using a monoclonal anti-PIVKA-II antibody as the immobilized antibody in an enzyme immunoassay using the two-antibody-sandwiching method.

2. The method of claim 1, wherein the assaying for PIVKA-II in a clinical specimen is performed after the specimen has been pre-treated by drying with dry filter paper for the screening of congenital dysoblism.

3. A composition of matter for use in an assay for determining PIVKA-II in a clinical specimen, said assay being an enzyme immunoassay using the two-antibody-sandwiching method, comprising an immobilized monoclonal anti-PIVKA-II antibody.

4. A kit for use to assay for PIVKA-II in a clinical specimen, said assay being an enzyme immunoassay using the two-antibody-sandwiching method, said kit containing, as an essential ingredient, immobilized monoclonal anti-PIVKA-II antibody.

* * * * *

UNITED STATES PATENT AND TRADEMARK OFFICE
CERTIFICATE OF CORRECTION

PATENT NO. : 4 780 410
DATED : October 25, 1988
INVENTOR(S) : Ichiro MATSUDA et al It is certified that error appears in the above-identified patent and that said Letters Patent is hereby corrected as shown below:

Column 10, line 21; change "dysoblism" to ---dysbolism---.

Signed and Sealed this

Twentieth Day of June, 1989

Attest:

DONALD J. QUIGG

Attesting Officer

Commissioner of Patents and Trademarks